Figure 1:
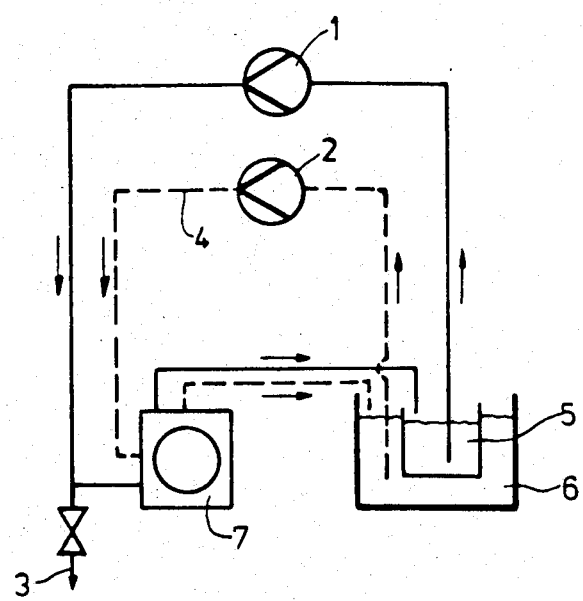

United States Patent [19]

von Bittera et al.

[11] Patent Number: 4,627,852
[45] Date of Patent: Dec. 9, 1986

[54] ACTIVE COMPOUND RELEASE SYSTEMS

[75] Inventors: Miklos von Bittera, Leverkusen; Rolf-Volker Meyer, Krefeld, both of Fed. Rep. of Germany

[73] Assignee: Bayer Aktiengesellschaft, Leverkusen, Fed. Rep. of Germany

[21] Appl. No.: 681,977

[22] Filed: Dec. 14, 1984

[30] Foreign Application Priority Data

Dec. 28, 1983 [DE] Fed. Rep. of Germany ....... 3347278

[51] Int. Cl.$^4$ ............................................. A61F 7/02
[52] U.S. Cl. ................................ 604/897; 128/156; 424/83; 604/304; 604/896; 604/897; 548/472; 548/491; 514/420; 514/336; 514/356; 514/406; 514/535; 514/404; 514/375; 514/222; 514/223; 514/448; 514/423; 514/424
[58] Field of Search ................... 128/156; 424/83, 274, 424/281; 604/304, 896, 897; 548/472, 491

[56] References Cited

U.S. PATENT DOCUMENTS 3,742,951 7/1973 Zaffaroni ........................ 128/268
4,031,894 6/1977 Urquhart et al. ................ 128/268
4,166,125 8/1979 Kigasawa et al. ................ 548/472
4,455,146 6/1984 Noda et al. ...................... 604/897

FOREIGN PATENT DOCUMENTS 0132690  2/1985  European Pat. Off. .
  77974 12/1970  Fed. Rep. of Germany ...... 548/491
3317285 12/1983  Fed. Rep. of Germany .
2021950 12/1979  United Kingdom .
2073588 10/1981  United Kingdom .
2085880  5/1982  United Kingdom ................ 548/491
2095108  9/1982  United Kingdom .

Primary Examiner—John Kight
Assistant Examiner—Kriellion Morgan
Attorney, Agent, or Firm—Sprung Horn Kramer & Woods

[57] ABSTRACT

In a therapeutic system such as a plaster for administration of an active compound through the skin and comprising a covering layer which is essentially impermeable to the active compound, an active coupound reservoir layer and a protective layer which can be pulled off and which is essentially impermeable to the active compound, the improvement wherein the reservoir layer contains about 1–30% of active compound in an elastomer mixture comprising a diene rubber which can optionally be copolymerized with an α-olefin, mixed with from 0 up to about 70% by weight of a polyisobutylene, polybutadiene oil and/or paraffin oil, and a tackifying resin. Thereby the active compound can be released in regulated relatively large quantity over a prolonged period of time.

15 Claims, 2 Drawing Figures

ACTIVE COMPOUND RELEASE SYSTEMS

The invention relates to a system for the release of active compounds to the skin over a prolonged period, in particular to antiphlogistic medical plasters.

U.S. Pat. No. 4,031,894 describes medical plasters which have a reservoir of a mixture of polyisobutenes of very different molecular weights, in particular molecular weights of 35,000–50,000 and 1,000,000–1,500,000, and mineral oils.

These plasters are suitable only for active compounds which are administered in very low doses. Scopolamine is mentioned in the U.S. patent specification.

DOS (German Published Specification) No. 3,007,368 describes plaster compositions which contain active compound and, as the polymer component, thermoplastic elastomers of the A—B—A or (A—B)$_n$X type, which largely contain vinyl-aromatics, preferably styrene, giving them thermoplastic processability.

Known active compound release systems, such as, for example, gels, ointments, known plasters and the like, allow only a limited absorption of active compound to the skin. The absorption depends on the base and the characteristics of the active compound.

An object of the present invention is thus to develop medical plasters with the aid of which regulated, relatively large therapeutically effective amounts of an active compound can be administered via the skin over a prolonged period. These plasters should be particularly suitable for administration of antiphlogistics. They should be compatible with the skin and with their aid it should be possible to administer high therapeutically effective doses of the active compound.

Surprisingly, it has now been found that corresponding plaster compositions with significantly increased rates of release of antiphlogistic active compounds are obtained if particular diene rubbers, which are optionally modified with olefins and can be mixed with up to 70% by weight of polyisobutylenes, are used as the polymer component.

The present invention thus relates to a therapeutic system for the administration of an active compound to the skin, containing a covering layer, a reservoir layer and a protective layer which can be pulled off, the reservoir layer containing a polymer component consisting of diene rubbers with at least 30% of the cis-1,4-linkage and Mooney viscosities of 20–100 (1+4 minutes running time at 100° C.), preferably of 30–70 (1+4 minutes running time at 100° C.), which can contain up to 50% of vinyl-aromatics incorporated either randomly or in blocks, by themselves or as a mixture with up to 70% by weight, of the polymer component, of polyisobutylenes and, besides entraining agent(s) and, if appropriate, tackifying resins, 1–30% by weight of antiphlogistics, as the active compounds.

The active compound-containing reservoir layer consists of 30–60% by weight of polymers, 30–60% by weight of entraining agent and of 2–40% by weight a tackifying resin, the sum of the three components adding up to 100% by weight.

The diene rubbers are known products which can be prepared on the basis of 1,3-dienes, such as butadiene, isoprene, piperylene or 2,3-dimethylbutadiene, preferably butadiene, in various ways which are known to the expert, the nature of the double bonds in the polymer being widely variable, depending on the choice of the metal catalyst (see, for example, Ullmanns Encyclopä die d. techn. Chemie (Ullmann's Encyclopaedia of Industrial Chemistry), 4th edition, volume 13, pages 602–611, Verlag Chemie, Weinheim/New York 1977).

Diene rubbers with over 80% of the cis 1,4-linkage are preferably used. Natural rubber is also suitable in the context of the parameters mentioned.

Examples of vinyl-aromatics which are suitable for combination with the diene rubbers are styrene, α-methylstyrene, vinyltoluenes, p-ethylstyrene, dimethylstyrenes and 4-vinyldiphenyl, preferably styrene. The diene rubbers modified with vinyl-aromatics are also known products, for example those known as "styrene/butadiene rubber", which can be prepared by known processes such that the vinyl-aromatics content is incorporated in the diene rubber not only randomly but also partly or predominantly as a block structure. The rubbers which can be used according to the invention have weight-average molecular weights $M_w$ of 20,000 to 2,000,000, preferably 20,000 to 500,000 g/mol.

Polyisobutylenes in the context of the invention are understood as polyisobutylenes which have a molecular weight distribution $M_w/M_n$, resulting from the preparation, of 1.5 to 3.5, preferably 2.0 to 3.0, and a viscosity average molecular weight—again as a result of the preparation—of 30,000 to 4,000,000 g/mol. The viscosity average polyisobutylenes to be used according to the invention is preferably 50,000 to 1,000,000 g/mol, particularly preferably 80,000 to 500,000 g/mol. The viscosity averages can be determined in a known manner as described in Polymer Handbook, J. Brandrup and F. H. Immergut, Wiley & Sons, New York, 1975, chapter IV, page 35.

Polybutadiene rubbers with Mooney viscosities of 30–60 (1+4 minutes running time at 100° C.), if appropriate mixed with 30–70% by weight of polyisobutylene with a molar weight distribution $M_w/M_n$ of 2.0–3.0, to improve comfort during wearing, are very particularly preferably used.

Entraining agents in the context of the present invention are understood as meaning oils, fatty acid esters, triglycerides, alcohols and/or fatty acids.

Oils in the context of the present invention are understood as meaning high-boiling aliphatic, araliphatic and/or aromatic hydrocarbons, preferably paraffin oil, Purcellin oil, perhydrosqualene and solutions of microcrystalline waxes in the oils, and mineral oils, preferably oils with a boiling range between 150° C. and 400° C.; and furthermore unsaturated hydrocarbons with at least 16 C atoms, such as, for example, oligomers of monoolefins, such as tetraisobutylene, pentaisobutylene and hexaisobutylene, or liquid polymers of diene(monoene) (co)polymers. Examples of liquid polymers of conjugated dienes are those of butadiene, isoprene, penta-1,3-diene, 2,3-dimethylbutadiene, copolymers of various dienes and liquid copolymers of a conjugated diolefin and small amounts of monoolefins, such as, for example, but-1-ene, isobutene, hex-1-ene, oct-1-ene and styrene, with molecular weights of 400 to 6,000, preferably 800 to 3,000, iodine numbers of 200 to 500 and viscosities of 100–10,000 cP at 50° C.

Liquid polybutadiene polymers which are at least 90% 1,4-linked, in which the content of cis-double bonds is more than 60% and which have molecular weights of 1,000 to 4,000 are particularly preferred.

Oils are also understood as meaning silicone oils of various viscosities, preferably with average molecular weights of 312 to 15,000, particularly preferably polydimethylsiloxanes.

Fatty acids esters are understood as meaning those which contain at least 12 C atoms, preferably 15 to 46 C atoms and particularly preferably 16 to 36 C atoms. By these there are understood, in particular: ethyl stearate, hexyl laurate, dipropylene glycol pelargonate, cetyl palmitate, isopropyl myristate, isopropyl palmitate, caprylic/capric acid esters of saturated fatty alcohols of $C_{12}$–$C_{18}$ chain length, isopropyl stearate, oleyl oleate, decyl oleate, ethyl oleate and synthetic duck uropygial gland fat, in each case individually or as a mixture.

Triglycerides are understood as meaning pure or mixed esters of glycerol and fatty acids of $C_8$–$C_{18}$ chain length, preferably caprylic and/or capric acid triglycerides.

Fatty acids are understood as meaning saturated or unsaturated fatty acids, preferably those with 12–24 C atoms, by themselves or as mixtures with one another, particularly preferably oleic acid.

Oils in the context of the invention are furthermore understood as meaning: sweet almond oil, avocado oil, sesame oil, castor oil, olive oil, grape seed oil, clove oil, groundnut oil, corn oil, hazelnut oil, jojoba oil, carthama oil and wheatgerm oil, in each case by themselves or as a mixture.

Resins in the context of the present invention are understood as meaning rosin, dehydrogenated rosin, glycerol esters of dehydrogenated rosin glycerol esters of rosin gum, hydrogenated rosin, glycerol esters of hydrogenated rosin, pentaerythritol esters of hydrogenated rosin, methyl esters of hydrogenated rosin, polymerised rosin, glycerol esters of polymerized rosin, terpene resins, coumarone/indene resins, hydrogenated petroleum resins, rosin modified by maleic anhydride and rosin derivatives, $C_5$-petroleum resins and half-esters of styrene/maleic acid copolymers, by themselves or as mixtures with one another. Polyterpene resins of alpha- or beta-pinene or modified glycerol esters of rosin are particularly preferred. Depending on the properties required in respect of tackiness and adhesion to the part onto which the resulting plaster is to be applied, these resins can be used either by themselves or in combination with one another.

Antiphlogistics in the context of the present invention are one or more antiphlogistics of the general formula I and/or II.

Antiphlogistics of the general formula I have the following structure:

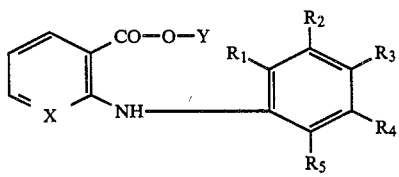

wherein
$R_1$–$R_5$ can be identical or different and denotes hydrogen, halogen, lower alkyl or substituted alkyl,
X denotes N or CH and
Y denotes hydrogen, metal ions, alkyl or substituted alkyl.

Halogen denotes fluorine, chlorine or bromine, preferably chlorine and/or bromine and particularly preferably chlorine. Lower alkyl is preferably alkyl with 1–6 C atoms, particularly preferably 1–4 C atoms, and substituted alkyl $R_1$–$R_5$ preferably denotes trihalogenoalkyl, particularly preferably trifluoromethyl. Metal ions are understood as meaning the ions of alkali metals, alkaline earth metals or aluminum preferably sodium. Substituted alkyl Y preferably denotes alkoxyalkyl, hydroxyalkyl, hydroxyalkoxyalkyl or trihalogenoalkyl, in which the number of C atoms is 1 to 6 and the alkyl chain can be straight or branched.

Antiphlogistics which are preferably used are those of the general formula I in which
$R_3$ and $R_4$ denote hydrogen,
X denotes nitrogen or a CH group,
Y denotes hydrogen, $C_1$–$C_4$-alkyl or substituted $C_1$–$C_4$-alkyl, hydroxyalkyl or hydroxyalkoxyalkyl with 1 to 6 C atoms and
$R_1$, $R_2$ and $R_5$ denote hydrogen, chlorine, $C_1$–$C_4$-alkyl or trifluoromethyl.

Particularly preferred antiphlogistics of the general formula I are those in which
X represents a CH group,
Y denotes hydrogen or hydroxyalkoxyalkyl with 1 to 6 C atoms and
$R_1$, $R_2$ and $R_5$ denote methyl, hydrogen, trifluoromethyl or chlorine.

The following antiphlogistics are very particularly preferred.

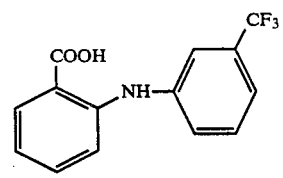

N—(α,α,α-Trifluoro-m-tolyl)-anthranilic acid = flufenamic acid

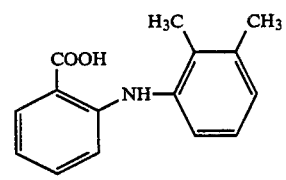

N—(2,3-Xylyl)-anthranilic acid

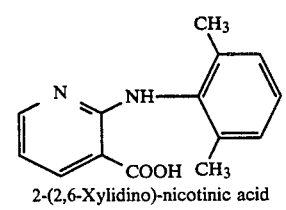

2-(2,6-Xylidino)-nicotinic acid

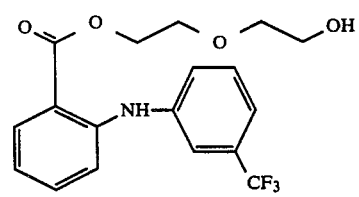

2-(2-Hydroxyethoxy)-ethyl N—(α,α,α-trifluoro-m-tolyl)-anthranilate = etofenamate Antiphlogistics in the context of the present invention are furthermore antiphlogistics of the general formula II having the structure:

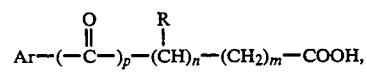

in which
R denotes hydrogen, lower alkyl or substituted alkyl,
Ar denotes aryl, heteroaryl, substituted aryl or substituted heteroaryl,
(n+m) denotes an integer and has the value zero, 1 or 2, and
p denotes zero or 1,
with the condition that Ar does not denote aryl or heteroaryl if n, m and p have the value of zero, and esters or amides thereof.

R preferably denotes lower alkyl radicals with 1–6 C atoms, preferably 1–4 C atoms, substituted alkyl, alkoxyalkyl or trihalogenoalkyl; aryl or heteroaryl, for example, phenyl, naphthyl, thiophenyl, pyrrolyl, indenyl, indolyl, benzothiazinyl or phenothiazinyl.

Substituents for aryl or heteroaryl are alkyl, preferably straight-chain or branched alkyl with up to 6 C atoms, alkoxy, hydroxyalkyl, acyl, hydroxyl, acetoxy, benzoyl, substituted benzoyl, phenyl, substituted phenyl, phenoxy, halogen, phenylalkenyl and phenylalkyl.

The esters are alkyl esters with 1–6 C atoms, preferably 1–4 C atoms in the alcohol component, particularly preferably methyl, ethyl, i- and n-propyl, substituted alkyl for example β-hydroxyethyl, esters of glycolic acid. The amides can also contain lower alkyl or substituted alkyl radicals in the grouping —CO—NH₂ instead of one or both of the amide hydrogens.

The following antiphlogistics of the general formula II are particularly preferred:

2-hydroxybenzoic acid
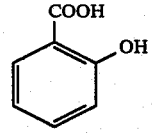

2-Acetoxybenzoic acid
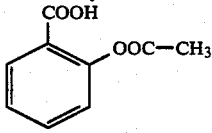

2′,4′-Difluoro-4-hydroxy-3-biphenylcarboxylic acid
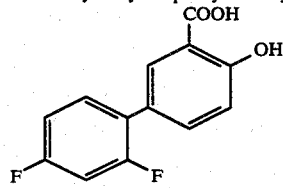

2-Hydroxybenzamide
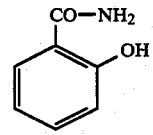

[2-(Aminocarbonyl)phenoxy]-acetic acid
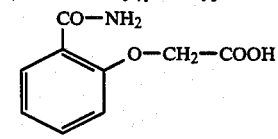

4-Allyloxy-3-chlorophenyl-acetic acid = alclofenac
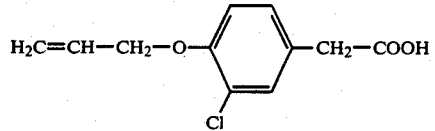

2-[(2,6-Dichlorophenyl)amino]-phenylacetic acid
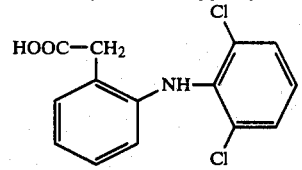

10-Methyl-phenothiazin-2-yl-acetic acid = metiazinic acid
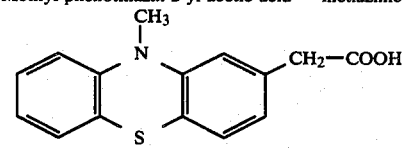

1-Methyl-5-(p-toluoyl)pyrrol-2-yl-acetic acid
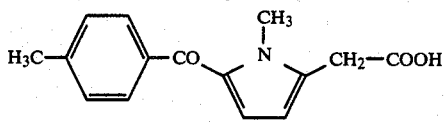

D—2-(6-Methoxy-2-naphthyl)-propionic acid = naproxen
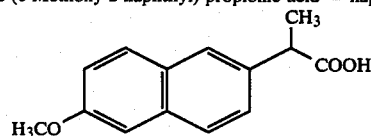

2-(p-Isobutylphenyl)-propionic acid
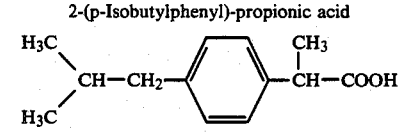

2-(3-Phenoxyphenyl)-propionic acid
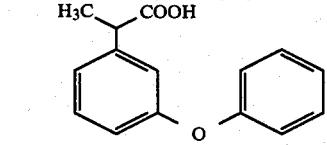

2-(m-Benzoylphenyl)-propionic acid = ketoprofen
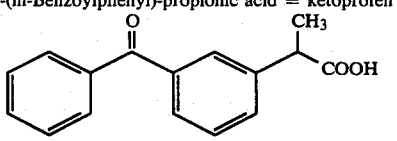

2-[4-(1-Oxo-2-isoindolinyl)-phenyl]-propionic acid = indoprofen
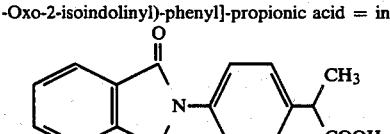

2-(2-Fluorobiphenyl-4-yl)-propionic acid
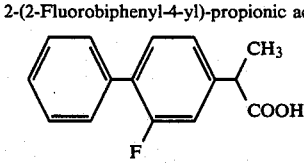

-continued 3-(4-Biphenylcarbonyl)-propionic acid

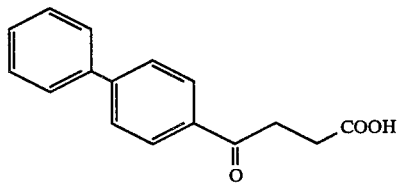

2-(5-Benzoyl-2-thienyl)-propionic acid

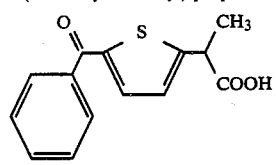

1-(p-Chlorobenzoyl)-5-methoxy-2-methylindole-3-acetic acid = indometacin

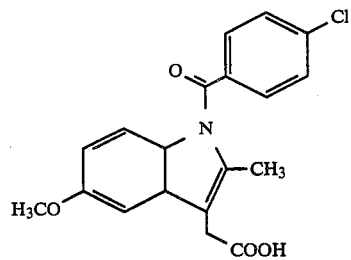

1-(p-Chlorobenzoyl)-5-methoxy-2-methylindole-3-acetoxyacetic acid = acemetacin

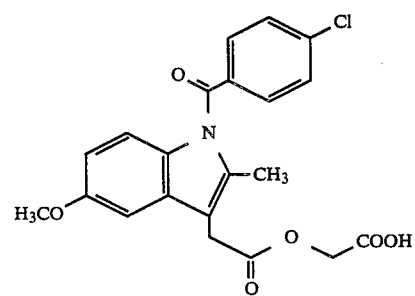

(Z)—5-Fluoro-2-methyl-1-([(3-methylsulfinyl)phenyl]-methylene-1H—indene-3-acetic acid

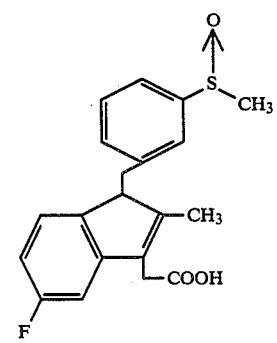

4-Butyl-1,2-diphenyl-3,5-pyrazolidine-dione = phenylbutazone

-continued 4-(3-Methyl-but-2-enyl)-1,2-diphenyl-pyrazolidine-3,5-dione = feprazone

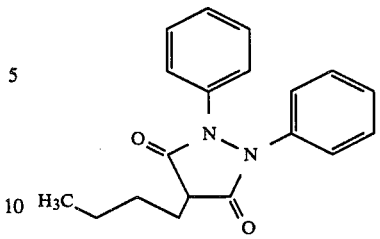

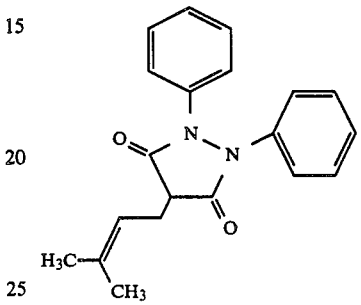

2-(4-Chlorophenyl)-α-methyl-5-benzoxazoleacetic acid = benoxaprofen

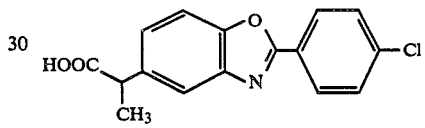

N—(2-thiazolyl)-2-methyl-4-hydroxy-2H—1,2-benzothiazine-3-carboxamide 1,1-dioxide

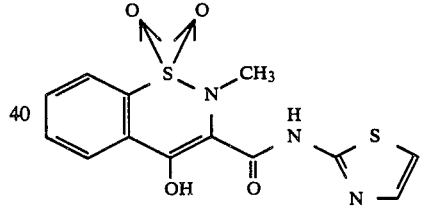

N—(2-pyridinyl)-2-methyl-4-hydroxy-2H—1,2-benzothiazine-3-carboxamide 1,1-dioxide (keto/enole mixture)

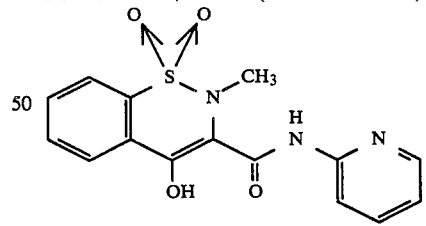

and alkyl esters and substituted alkyl esters thereof.

Either one or more of the abovementioned antiphlogistics of the general formullae I and II can be incorporated into the plasters.

The antiphlogistics can be incorporated into the reservoir layer in an amount of 1-30% by weight, preferably 2-20% by weight. The % by weight given relates to the total reservoir.

Other active substances or cooling or fragrance-releasing substances, preferably methyl salicylate, glycol salicylate, salicylic acid, menthol, peppermint oil, camphor, thymol, Acrinol, scopola extract, chloropeniramine maleate, benzyl nicotinate, capsicum extract, nonylvanillylamide and capsaicin, can also additionally be added to these antiphlogistics.

If necessary, additives and fillers, for example antiageing agents, antioxidants and reinforcing fillers, can be added to the plasters according to the invention as long as the gel-like properties are not destroyed.

Known active compound release systems, such as, for example, gels, ointment bases and plasters, release about 0.5–5 mg of active compound in 4 hours. In contrast, the therapeutic system according to the invention described above releases up to 18 mg of active compound in 4 hours, with a significantly greater bioavailability. The rate of release of the active compound from the systems according to the invention can be adjusted to almost any desired value by changing the polymer content, the entraining agent or the resin.

The reservoir containing the active compound and the plaster based thereon can be produced, for example, as follows: the plaster bases (polymer, resin and entraining agent) are introduced into a suitable dissolving vessel and are dissolved in benzine, with stirring. A clear to slightly turbid solution 1 results. The active compound component is also dissolved in a suitable solvent, and the solution is added to polymer solution 1.

The resulting solution 2 containing active compound is applied uniformly to siliconized paper and drawn to a film. The coated paper with the plaster base is dried in air for 24 hours and then kept in a circulating air drying cabinet at 40° C. for 1 hour.

The rates of release of active compound are determined in an absorption model described in more detail in the experimental section. (FIGS. 1 and 2).

In FIG. 1 (1) represents a hose pump for the acceptor, (2) a hose pump for heating, (3) sample withdrawal, (4) circulation for heating liquid, (5) the acceptor medium, (6) the heating vessel and (7) the resorption cell with membrane.

Figure 2:
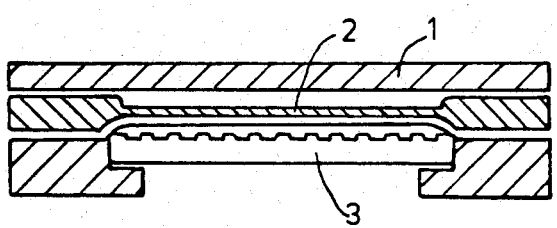

In FIG. 2 (1) represents an opaque cell material, (2) a membrane and (3) a viewing window of glass, also corrugated plate for the acceptor medium.

TESTING IN VITRO OF THE RELEASE OF THE PLASTERS ACCORDING TO THE INVENTION

All the plasters were produced in the same manner, with 10% of active compound component, from polymer, entraining agent, resin and, if appropriate, solvent (benzene, hexane or a hexane/toluene mixture). The particular proportions used are given in the recipe descriptions.

For this, all the components were dissolved or suspended. Acetone and/or ethanol were chiefly used as the solvents for the active compound.

These solutions or suspensions were processed to films 50–150 μm thick.

Experimental parameters:
acceptor medium: mixture of water ethanol, PVP and sorbitan fatty acid ester
volume of the acceptor medium: 200 ml
temperature of the acceptor medium: 35°–36° C.
pump capacity: 16 ml/minute (apparatus constant)
membrane: the film described in Example 3 of DE-OS (German Published Specification) No. 3,312,735 was used as the membrane
Absorption area: 33.18 cm² (cell constant)

The acceptor medium was heated to the required temperature in a stock vessel and pumped around the absorption cells via tubes. Samples were withdrawn between the pump and the absorption cells. Sampling was effected at specified intervals of time. In each case 6 ml of sample were withdrawn and measured by spectrophotometry. The acceptor liquid was not replaced, since this would mean a dilution of the remainder.

CALCULATION OF THE RESULTS

A calibration curve was first recorded for the particular active compound component, with the aid of which the active compound concentration (mg or %) in the individual samples was determined from the extinction values measured for the individual samples. The extinctions were measured by UV spectroscopy.

To calculate the "relative absorption" (proportion of "absorbed" active compound of the total content of the plaster in %), it is necessary to know the amount of active compound employed. The content of active compound of a defined plaster size (33.18 cm²) is known from the production of the plaster.

The concentration of active compound in the sample was determined from the extinction values measured for the individual samples, with the aid of a calibration line or the factor determined therefrom.

Calculation was effected by the following formulae $$M_f(t) = V_t \cdot C_i + M_F(t) \; [mg]$$

$$M_F(t) = \sum_{i=0}^{i=n-1} (V_D \cdot C_i) \; [mg]$$

$M_f(t)$: amount of drug released up to time t [mg]
$V_t$: volume of the acceptor at time t [ml]
$C_i$: active compound concentration in the individual sample [mg/ml]
$M_F(t)$: amount of active compound removed up to time t [mg]
$V_D$: sample volume [ml]
n: number of samples up to time t
t: duration of the experiment

DESCRIPTION OF THE PREPARATION

The active compound release systems according to the invention were produced as follows: the mixture of polymer resin and entraining agent were prekneaded in a Z-kneader at a temperature of 120° to 150° C. When the mass was a homogeneous melt, the active compound was homogeneously incorporated, while gassing with nitrogen. The melt containing active compound was applied to the carrier film (kneader).

The active compound release systems according to the invention were dissolved in a solvent mixture and the solution was applied to the carrier film and then dried (solution).

EXAMPLE SERIES A

Standard (not according to the invention)

In this series of experiments, a styrene/isoprene/styrene TR block copolymer ("Cariflex TR 1107", from Shell Chemical Company) was used as the polymer, thinly liquid paraffin was used as the entraining agent and a polyterpene resin from β-pinene was used as the tackifying resin.

The styrene/isoprene/styrene TR block copolymer plaster containing 10% of active compound was used as the reference standard in all the further experiments.

The precise composition of the plaster base is given in Table 1. The plaster was produced as described above. The rates of release are described in Table 2.

TABLE 1

| Composition of the standard formulation | |
|---|---|
| Styrene/isoprene/styrene/TR block copolymer | 36.0 g |
| Thinly liquid paraffin | 45.0 g |
| Polyterpene resin from β-pinene | 9.0 g |
| Etofenamate | 10.0 g |

TABLE 2

Release from the experimental standard series as a function of time

| Standard | Amount of etofenamate released in mg/hour | | | | | | % | Amount of etofenamate weighed out in mg |
|---|---|---|---|---|---|---|---|---|
| | 0.5 | 1 | 1.5 | 2 | 3 | 4 | | |
| 10% | 1.44 | 2.16 | 2.70 | 3.24 | 4.63 | 4.81 | 21.20 | 22.77 |

EXAMPLE SERIES B

In this series of experiments, the composition of the polymers was varied. The precise designation is given in Table 3. The plasters were produced as described above. The amounts of all the polymers listed in Table 3 were varied in accordance with the following scheme, the paraffin oil and resin content remaining constant:

| | A1 | A2 |
|---|---|---|
| Polymer | 36.0 g | 45.0 g |
| Thinly Liquid paraffin oil | 45.0 g | 37.5 g |
| Polyterpene resin from β-pinene | 9.0 g | 7.5 g |
| Etofenamate | 10.0 g | 10.0 g |

The rates of release are described in Table 4.

TABLE 3

Example series B: Description of the polymers used

| No.[1] | Description |
|---|---|
| 01 x | Styrene/butadiene rubber (solution SBR) with 18% of styrene, Mooney viscosity (1 + 4) minutes running time, 100° C.:35 |
| 02 x | Styrene/butadiene block copolymer prepared with a Li catalyst, styrene content 30%, 22% of which is in block form, molecular weight about 180,000 g/mol |
| 03 x | Polybutadiene rubber, 93% cis 1,4 content, 4% 1,2 content, prepared with a Ti catalyst, Mooney viscosity (1 + 4) minutes running time, 100° C.:35 |
| 04 x | Polybutadiene rubber, 38% cis 1,4 content, 10% 1,2 content, prepared with a Li catalyst, Mooney viscosity (1 + 4) minutes running time, 100° C.:35 |
| 05 x | Polybutadiene rubber, 38% cis 1,4 content, 10% 1,2 content, prepared with a Li catalyst, Mooney viscosity (1 + 4) minutes running time, 100° C.:55 |

[1]The first two figures designate the polymer, the designation of the formulation appears instead of x (see above, A1, A2).

TABLE 4

Example series B: release as a function of time

| No. | Etofenamate released (mg) in hours | | | | | | % | Amount of etofenamate weighed out in mg |
|---|---|---|---|---|---|---|---|---|
| | 0.5 | 1 | 1.5 | 2 | 3 | 4 | | |
| Standard | 1.44 | 2.16 | 2.70 | 3.24 | 4.63 | 4.81 | 21.20 | 22.77 |
| 01A1 | 3.37 | 5.79 | 8.14 | 9.62 | 12.05 | 13.87 | 54.97 | 25.23 |
| 01A2 | 2.91 | 5.23 | 7.05 | 8.45 | 11.50 | 13.93 | 44.00 | 31.94 |
| 02A1 | 2.50 | 4.43 | 6.25 | 7.92 | 10.79 | 13.09 | 51.66 | 25.34 |
| 02A2 | 2.65 | 4.33 | 6.11 | 7.55 | 10.42 | 12.50 | 51.74 | 24.16 |
| 03A1 | 3.11 | 6.67 | 8.83 | 10.41 | 13.86 | 15.81 | 75.56 | 20.03 |
| 03A2 | 2.65 | 4.43 | 6.16 | 7.46 | 10.11 | 12.23 | 37.47 | 32.64 |
| 04A1 | 3.72 | 6.25 | 8.40 | 9.75 | 12.94 | 14.84 | 63.73 | 23.29 |
| 04A2 | 2.14 | 3.62 | 5.54 | 7.03 | 10.13 | 12.34 | 48.02 | 25.69 |
| 05A1 | 2.70 | 4.03 | 5.25 | 6.51 | 8.62 | 10.35 | 33.41 | 30.98 |
| 05A2 | 3.01 | 5.04 | 6.81 | 8.67 | 11.23 | 13.22 | 40.74 | 32.45 |

EXAMPLE SERIES C

Variation of the liquid component

The liquid component of the formulations selected from Example series B was changed in composition according to the following scheme, the remaining recipe being retained.

| | B1 | B2 |
|---|---|---|
| Polymer | as in Example series B | |
| Liquid component | Polybutadiene oil of molecular weight 1,500 | Polybutadiene oil of molecular weight 1,500 + thinly Liquid paraffin 1:1 |
| Resin | as in Example series B | |
| Etofenamate | 10% | 10% |

The precise composition of the plaster base is given in Table 5 and the rates of release are given in Table 6.

TABLE 5

Example series C: Variation of the Liquid component, composition of the formulations

| No. | Polymer | liquid component Polybutadiene oil, molecular weight 1,500 | Thinly Liquid paraffin | Resin | Etofenamate |
|---|---|---|---|---|---|
| 03A1 | 36% | — | 45% | 9% | 10% |
| 03B1 | 36% | 45% | — | 9% | 10% |
| 03B2 | 36% | 22.5% | 22.5% | 9% | 10% |
| 04A1 | 36% | — | 45% | 9% | 10% |
| 04B1 | 36% | 45% | — | 9% | 10% |
| 04B2 | 36% | 22.5% | 22.5% | 9% | 10% |

TABLE 6

Example series C: Release as a function of time

| No. | Etofenamate released (mg) in Hours | | | | | | Amount of etofenamate weighed out in mg |
|---|---|---|---|---|---|---|---|
| | 0.5 | 1 | 1.5 | 2 | 3 | 4 % | |
| Standard | 1.44 | 2.16 | 2.70 | 3.24 | 4.63 | 4.81 21.20 | 22.77 |
| 03A1 | 3.31 | 5.79 | 8.14 | 9.62 | 12.05 | 13.87 54.97 | 25.23 |
| 03B1 | 3.67 | 6.59 | 9.17 | 11.41 | 14.64 | 16.41 71.06 | 23.03 |
| 03B2 | 3.37 | 6.14 | 8.25 | 10.33 | 13.43 | 15.46 72.79 | 21.25 |
| 04A1 | 3.72 | 6.25 | 8.40 | 9.75 | 12.94 | 63.73 63.73 | 23.29 |
| 04B1 | 1.22 | 2.50 | 4.09 | 5.44 | 8.27 | 37.94 37.94 | 29.31 |
| 04B2 | 1.63 | 2.97 | 4.50 | 5.80 | 8.63 | 38.63 38.63 | 29.54 |

EXAMPLE SERIES D

Polymer mixtures and variation of the active compounds

Example 1 (solution)

Styrene/butadiene rubber (solution SBR): 36.0 g
Thinly liquid paraffin: 45.0 g
Polyterpene resin from β-pinene: 9.0 g
Etofenamate: 10.0 g
Release: 13.9 mg (54.97%) after 4 hours.

Example 2 (solution)

Styrene/butadiene block copolymer, styrene content 30%, 22% in block form, molecular weight about 180,000 g/mol: 45.0 g
Thinly liquid paraffin: 37.5 g
Polyterpene resin from β-pinene: 9.0 g
Etofenamate: 10.0 g
Release: 12.5 mg (51.74%) after 4 hours.

Example 3 (kneader)

Styrene/butadiene block copolymer, styrene content 30%, 22% in block form, molecular weight about 180,000 g/mol: 36.0 g
Polybutadiene oil of molecular weight 1,500: 45.0 g
Polyterpene resin from β-pinene: 9.0 g
Etofenamate: 10.0 g
Release: 16.41 mg (71.06%) after 4 hours.

Example 4 (kneader)

Polybuadiene rubber, 93% cis 1,4 content, 4%, 1,2 content, Mooney viscosity 35: 36.0 g
Decyl oleate: 45.0 g
Modified glycerol ester of rosin: 9.0 g
Acemetacin: 10.0 g
Release: 9.5 mg (41.7%) after 4 hours.

Example 5 (solution)

Polybutadiene rubber, 38% cis 1,4 content, 10% 1,2 content,
Mooney viscosity 35: 45.0 g
Thinly liquid paraffin: 37.5 g
Polyterpene resin from β-pinene: 7.5 g
Etofenamate: 10.0 g
Release: 12.34 mg (48.02%) after 4 hours.

Example 6 (solution)

Polybutadiene rubber, 38% cis 1,4 content, 10% 1,2 content, Mooney viscosity 35: 36.0 g
Thinly liquid paraffin: 45.0 g
Polyterpene resin from β-pinene: 9.0 g
Etofenamate: 10.0 g
Release: 18.84 mg (63.73%) after 4 hours.

Example 7 (solution)

Polybutadiene rubber, 38% cis 1,4 content, 10% 1,2 content, Mooney viscosity 35: 36.0 g
Thinly liquid paraffin: 45.0 g
Polyterpene resin from β-pinene: 9.0 g
Ketoprofen: 10.0 g
Release: 12.55 mg (52.8%) after 4 hours.

Example 8 (solution)

Polyisobutylene of molecular weight 400,000: 22.5 g
Polybutadiene rubber, 38%, 1,4 content, 10% 1,2 content, Mooney viscosity 35: 22.5 g
Thinly liquid paraffin: 37.5 g
Modified glycerol ester of rosin: 7.5 g
Etofenamate: 10.0 g
Release: 12.45 mg (48.7%) after 4 hours.

Example 9 (solution)

Styrene/butadiene rubber (solution SBR) with 18% of styrene: 36.0 g
Thinly liquid paraffin: 45.0 g
Modified glycerol ester of rosin: 9.0 g
Ketoprofen: 10.0 g
Release: 10.7 mg (42.6%) after 4 hours.

Example 10 (solution)

Polyisobutylene of molecular weight 400,000: 22.5 g
Polybutadiene rubber, 38% cis 1,4 content, 10% 1,2 content, Mooney viscosity 35: 22.5 g
Thinly liquid paraffin: 37.5 g
Polyterpene resin from α-pinene: 7.5 g
Acemetacin: 10.0 g
Release: 10.27 mg (33.8%) after 4 hours.

It will be understood that the specification and examples are illustrative but not limitative of the present invention and that other embodiments within the spirit and scope of the invention will suggest themselves to those skilled in the art.

We claim:

1. In a medical plaster comprising a covering layer which is essentially impermeable to the active compound, an active compound reservoir layer and a protective layer which can be pulled off and which is essentially impermeable to the active compound, the improvement wherein the reservoir layer contains about 1–30% of active compound comprising an antiphlogistic in an elastomer mixture comprising a diene rubber which can optionally be randomly copolymerised with an α-olefin, mixed with from 0 up to about 70% by weight of a polyisobutylene, polybutadiene oil and/or paraffin oil, and a tackifying resin.

2. In a therapeutic system comprising a medical plaster for adminstration of an active compound comprising an antipholgistic through the skin, and comprising a covering layer, a reservoir layer which contains the active compound and also contains a polymer, an entraining agent, a resin and a protective layer which can be pulled off, the improvement wherein the polymer of the reservoir layer containing active compounds is diene rubber with at least 30% of the cis 1,4-linkage and a Mooney viscosity (1+4 minutes running time, 100° C.) of about 20–100, which can contain up to 50% of a vinyl-aromatic incorporated randomly, mixed with from 0 up to about 70% by weight of the polymer component of polyisobutylene, the reservoir containing about 1–30% by weight of an antiphlogistic as the active compound.

3. A medical plaster according to claim 1, wherein the reservoir containing active compound comprises about 30–60% by weight of polymer, 30–60% by weight of entraining agent and 2–40% by weight of resin, in addition to the active compound.

4. A medical plaster according to claim 1, wherein the diene rubber comprises butadiene and/or isoprene copolymerised with up to 50% by weight of a vinyl-aromatic.

5. A medical plaster according to claim 1, wherein the diene rubber comprises a polybutadiene rubber with 30–40% of cis 1,4- and 40–60% of trans 1,4 double bonds and a Mooney viscosity of 30–50.

6. A medical plaster according to claim 1, wherein the diene rubber comprises a polybutadiene rubber with more than 80% cis 1,4 content and a Mooney viscosity of 35–55.

7. A medical plaster according to claim 1, wherein the diene rubber comprises a styrene/butadiene rubber with 15–30% by weight of styrene in the polymer and a Mooney viscosity of 30–50.

8. A medical plaster according to claim 1, wherein the diene rubber is mixed with a polyisobutylene with a molecular weight distribution $M_w/M_n$ of 1.5 to 3.5, and an average molecular weight of 30,000 to 4,000,000 g/mol.

9. A therapeutic system according to claim 2, wherein at least one of a paraffin oil and a liquid polybutadiene oil is used as the entraining agent.

10. A medical plaster according to claim 1, wherein the active compound is selected from the group consisting of an antiphlogistic of the formula

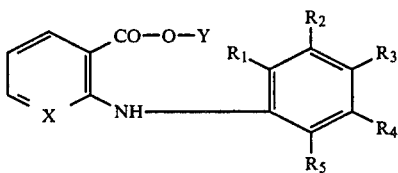

and

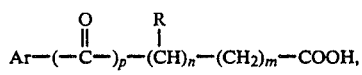

and esters and amides thereof, in which $R_1$–$R_5$ each independently is hydrogen, halogen, lower alkyl or substituted alkyl, X is N or CH, Y is hydrogen, a metal ion, alkyl or substituted alkyl, R is hydrogen, lower alkyl or substituted alkyl, Ar is aryl, heteroaryl, substituted aryl or substituted heteroaryl, n and m each is an integer and together total zero, 1 or 2, and p is zero or 1, with the proviso that Ar is not aryl or heteroaryl if n, m and p each is zero.

11. A medical plaster according to claim 1, wherein the active compound is etofenamat.

12. A medical plaster according to claim 1, wherein the active compound is ketoprofen.

13. A medical plaster according to claim 1, wherein the active compound is acematacin.

14. A medical plaster according to claim 1, wherein the active compound is indoprofen.

15. A medical plaster according to claim 1, wherein the active compound is indometacin.

* * * * *